(12) United States Patent
Tucker et al.

(10) Patent No.: US 7,142,904 B1
(45) Date of Patent: Nov. 28, 2006

(54) METHOD AND COMPOSITION FOR PROBING THE BODY THROUGH THE SKIN

(75) Inventors: Don Tucker, Eugene, OR (US); Phan Luu, Eugene, OR (US)

(73) Assignee: Electrical Geodesics, Inc., Eugene, OR (US)

( * ) Notice: Subject to any disclaimer, the term of this patent is extended or adjusted under 35 U.S.C. 154(b) by 0 days.

(21) Appl. No.: 10/369,489

(22) Filed: Feb. 19, 2003

Related U.S. Application Data

(63) Continuation-in-part of application No. 09/803,085, filed on Mar. 8, 2001, now Pat. No. 6,529,759.

(51) Int. Cl.
A61B 5/05 (2006.01)
(52) U.S. Cl. ...................... 600/407; 600/453
(58) Field of Classification Search ............... 600/365, 600/391–393, 396–397, 407–414, 453, 425, 600/473, 310, 392, 342, 365.1; 604/20; 607/152–153; 156/242; 264/28, 101, 154; 424/78.2, 78.06, 487; 524/90, 505; 73/633; 128/660.1; 356/342
See application file for complete search history.

(56) References Cited

U.S. PATENT DOCUMENTS

| | | | | |
|---|---|---|---|---|
| 3,993,049 A | * | 11/1976 | Kater ........................ | 600/391 |
| 4,123,654 A | * | 10/1978 | Reiss et al. ............ | 250/363.04 |
| 4,436,684 A | | 3/1984 | White | |
| 4,474,570 A | * | 10/1984 | Ariura et al. ................. | 604/20 |
| 4,532,591 A | | 7/1985 | Osterholm | |
| 4,608,635 A | | 8/1986 | Osterholm | |
| 4,774,957 A | * | 10/1988 | Nambu et al. .............. | 600/414 |
| 4,848,351 A | * | 7/1989 | Finch ........................ | 600/391 |
| 4,922,915 A | * | 5/1990 | Arnold et al. .............. | 600/546 |
| 5,039,774 A | * | 8/1991 | Shikinami et al. .......... | 600/437 |
| 5,065,742 A | * | 11/1991 | Belikan et al. ............. | 600/439 |
| 5,165,410 A | * | 11/1992 | Warne et al. .......... | 250/363.04 |
| 5,291,888 A | * | 3/1994 | Tucker ........................ | 600/383 |
| 5,330,527 A | * | 7/1994 | Montecalvo et al. ....... | 600/392 |
| 5,348,006 A | * | 9/1994 | Tucker | |
| 5,390,110 A | | 2/1995 | Cheney et al. | |
| 5,465,284 A | * | 11/1995 | Karellas ................... | 250/252.1 |
| 5,482,034 A | | 1/1996 | Lewis | |
| 5,630,422 A | | 5/1997 | Zanakis | |
| 5,718,230 A | * | 2/1998 | Chapman et al. ........... | 600/453 |
| 5,719,399 A | | 2/1998 | Alfano et al. | |
| 5,807,251 A | | 9/1998 | Wang et al. | |
| 5,810,742 A | * | 9/1998 | Pearlman .................... | 600/547 |
| 5,813,984 A | | 9/1998 | Haaga et al. | |
| 5,825,488 A | * | 10/1998 | Kohl et al. ................. | 600/310 |
| 5,830,146 A | * | 11/1998 | Skladnev et al. ........... | 600/478 |
| 5,853,370 A | | 12/1998 | Chance et al. | |
| 5,902,235 A | | 5/1999 | Lewis et al. | |
| 5,941,834 A | * | 8/1999 | Skladnev et al. ........... | 600/587 |
| 5,999,836 A | * | 12/1999 | Nelson et al. .............. | 600/407 |
| 6,041,094 A | * | 3/2000 | Russell ....................... | 378/162 |
| 6,175,752 B1 | * | 1/2001 | Say et al. ................... | 600/345 |
| 6,216,540 B1 | * | 4/2001 | Nelson et al. ................ | 73/633 |
| 6,330,470 B1 | * | 12/2001 | Tucker et al. ............... | 600/544 |

(Continued)

*Primary Examiner*—Tu Hoang
(74) *Attorney, Agent, or Firm*—Birdwell & Janke, LLP

(57) ABSTRACT

A method and composition for probing the body through the skin. In one embodiment of the invention, the method includes providing a medium for interfacing with the skin, applying the medium to the skin at a selected location, and coupling at least two of (a) an electric signal, (b) an acoustic signal, and (c) an optical signal through the skin and through the medium at the selected location.

23 Claims, 1 Drawing Sheet

U.S. PATENT DOCUMENTS

| | | | |
|---|---|---|---|
| 6,405,069 B1 * | 6/2002 | Oraevsky et al. | 600/316 |
| 6,410,645 B1 * | 6/2002 | Pathak et al. | 525/90 |
| 6,517,497 B1 * | 2/2003 | Rymut et al. | 600/538 |
| 6,529,759 B1 * | 3/2003 | Tucker et al. | 600/407 |
| 6,639,014 B1 * | 10/2003 | Pathak et al. | 525/90 |
| 6,719,699 B1 * | 4/2004 | Smith | 600/459 |
| 6,761,878 B1 * | 7/2004 | Achilefu et al. | 424/9.6 |
| 6,827,716 B1 * | 12/2004 | Ryan et al. | 606/41 |

* cited by examiner

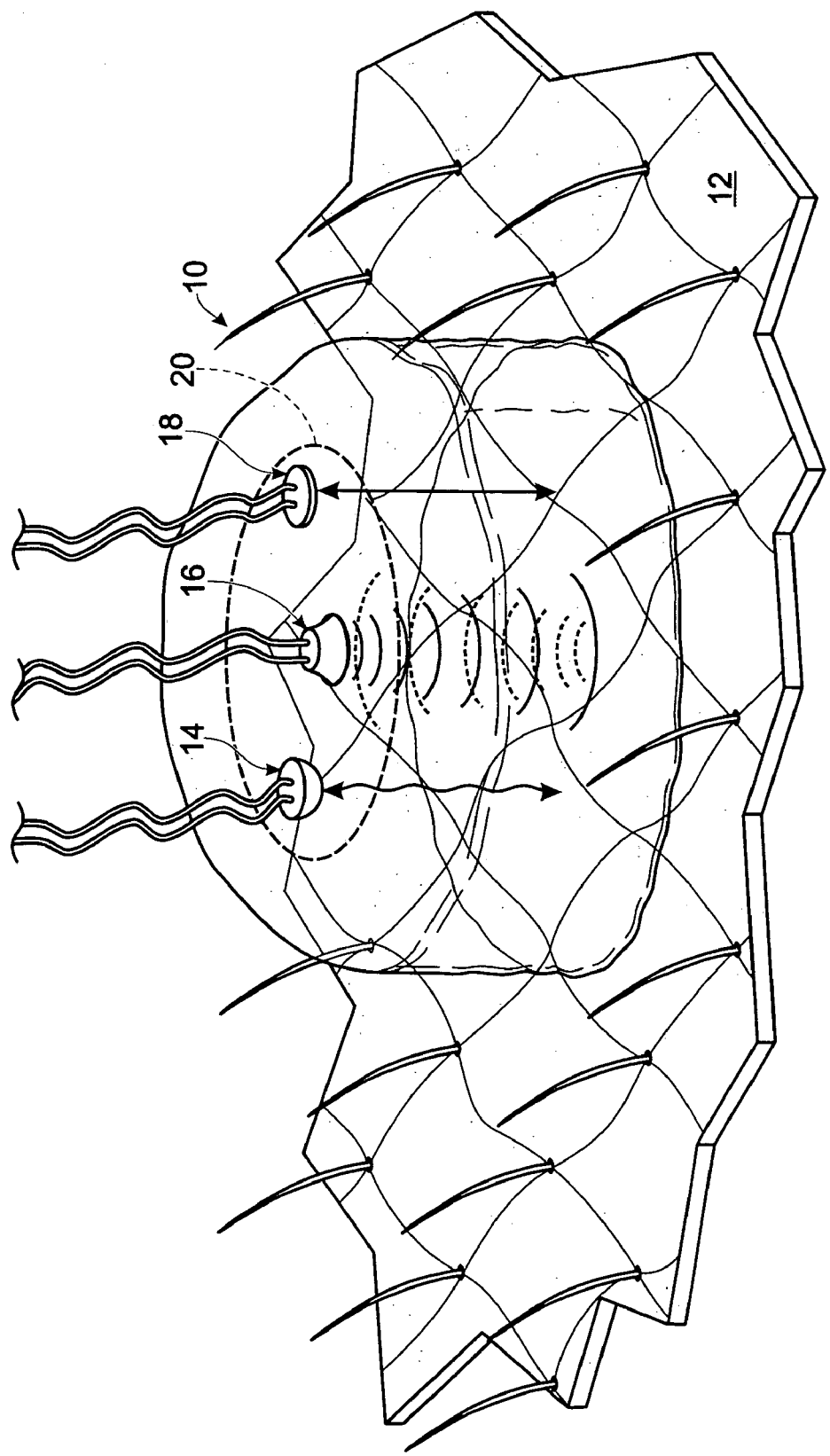

METHOD AND COMPOSITION FOR PROBING THE BODY THROUGH THE SKIN

REFERENCE TO RELATED APPLICATIONS

This is a continuation-in-part of U.S. Ser. No. 09/803,085, filed Mar. 8, 2001, now U.S. Pat. No. 6,529,759 the specification of which is incorporated by reference herein.

FIELD OF INVENTION

The present invention relates to a method and composition for probing the body through the skin. More particularly, the invention relates to coupling multi-modal signals to the skin, such as a combination of electric, acoustic and optical signals.

BACKGROUND OF INVENTION

In the medical arts and sciences, it is routinely required to probe internal parts of the body by coupling signals of various signal types to the skin, for transmitting the signals through the skin and into the body, or for receiving signals through the skin for input to a signal measuring or analyzing device. This may be for the purpose of imaging or source localization, or for stimulating internal tissue.

For example, in electroencephalography ("EEG") and electrocardiography ("ECG"), surface electrodes placed on the skin receive electric signals generated from within the body to probe the electrical output of the brain and heart, respectively. Conversely, electric signals are transmitted through the skin and into the body in electrical impedance tomography ("EIT"), to probe the body in a stimulative sense for the purpose of obtaining images.

An advantage recognized by one of the present inventors and that has been described in U.S. Pat. No. 6,330,470 to Tucker, Ferree and Ericksen, incorporated by reference herein, results from placing a transmitting or stimulating electrode at the same location as a receiving electrode for more efficiently locating electrical sources in the body as well as for more precisely and efficiently imaging the body.

It is also common practice to probe the body in a stimulative sense with acoustic signals, such as in ultrasound diagnostic imaging ("UI"), and to a lesser extent optical signals, such as in near-infrared spectroscopy and optical tomography ("NIR OT").

Each of these signal types, i.e., electrical, acoustical, and optical, provides particular advantages and disadvantages for probing the body. Accordingly, in the prior art, one of the signal types has been selected in preference to the others to suit the particular purpose at hand. For example, EIT employs electric signals to probe the electrical characteristics of the body, particularly conductive properties. NIR OT uses near-infrared electromagnetic signals, i.e., light-waves, which propagate with minimal absorption through soft tissue. These are particularly useful to image hard tissue such as bone. On the other hand, acoustic signals are useful for imaging soft tissue.

As explained in the '470 patent, localizing sources of electrical activity within the body by analyzing fields outside the body is computationally difficult, and for the technique to be effective, it is necessary to reduce ambiguities as much as possible. This can be done by increasing the number of electrodes, but this is costly, and where the electrodes must each be placed on the body, time consuming. Improving resolution in imaging processes also has generally required a greater density of sensing hardware and improved control and precision of probe signal application, which pushes the limits of allowable cost and available technology. The conventional practice of selecting one imaging method for a particular imaging circumstance or need has ensured that the cost and technological limitations of the different types of probing are retained.

Accordingly, there is a need for a method and composition for probing the body through the skin that recognizes the advantages of combining imaging methodologies in overcoming the limitations of the individual imaging methodologies.

BRIEF SUMMARY OF THE INVENTION

A method and composition for probing the body through the skin according to the present invention is described. Particularly described is a method for probing interior portions of a body through the skin, which includes providing a medium for interfacing with the skin, applying the medium to the skin at a selected location, and coupling at least two of (a) an electric signal, (b) an acoustic signal, and (c) an optical signal through the skin and through the medium at the selected location.

Preferably, the interfacing medium includes a hydrogel, and preferably the hydrogel is thermoresponsive.

Preferably, the interfacing medium has a minimum conductivity of about 1.0 (ohm-meter)$^{-1}$.

Preferably, the interfacing medium has an acoustic impedance of about 1.5+/−0.15 kg/s-m$^2$.

Preferably, the interfacing medium has a refractive index of about 1.5+/−0.15.

Accordingly, it is an object of the present invention to provide a novel and improved method for probing and composition the body through the skin.

The foregoing and other objectives, features, and advantages of the invention will be more readily understood upon consideration of the following detailed description of the invention, taken in conjunction with the accompanying drawing.

BRIEF DESCRIPTION OF THE DRAWING

The FIGURE is a pictorial view of a medium for coupling a signal to the skin, according to a method for probing the body through the skin according to the present invention.

DETAILED DESCRIPTION OF A PREFERRED EMBODIMENT

A method and composition for probing the body according to the present invention recognizes the advantages of coupling multi-modal signals into and out of the body through the skin, as well as the advantages of a skin interfacing medium that simultaneously optimizes such coupling.

The term "multi-modal" refers to multiple modes of signal propagation, such as electrical, acoustic and electromagnetic modes of propagation. For example, electric signals propagate by being conducted by electrically conductive tissue, and by capacitive and inductive coupling with electrically conductive tissue. Acoustic signals propagate through non-electrically conductive materials by mechanical deformations in the material. Electromagnetic signals need no medium through which to propagate, but propagation is affected by electronic polarization in the material. Typical electromagnetic signals used to probe body tissue are X-rays and light.

These different signal modes are typically provided at different frequencies as well. The frequency of electric signals used for stimulating body tissue in EIT are on the order of 1 Hz–100 KHz, while the ultrasonic signals used in UI have frequencies on the order of 1–20 MHz, and the near infra-red light used in NIR OT has a wavelength that may range from about 0.5 µm to about 2.5 µm, and which preferably ranges from about 650–850 nm, corresponding to frequencies on the order of $10^5$ GHz. Generally, higher frequencies provide greater resolution, but lower frequencies may provide advantages in terms of depth of penetration, as in acoustic imaging.

Probing internal body tissue through the skin is typically for the purpose of characterizing the impedance of the tissue (where the term "impedance" is used in its most general sense), localizing sources of electrical activity in the tissue, and imaging the tissue from outside the body. However, probing according to the present invention may be performed for any desired purpose.

In general, the location, size and nature of internal tissue structures are recognized as a result of the structures' interaction with signals applied through the skin, such as in imaging and impedance characterization, or as a result of signals the structures themselves emit through the skin, as in source localization. In the fields of impedance characterization and source localization, this process is known as solving the "inverse problem."

The inverse problem is generally to characterize internal body structures from signals propagating from those structures to points of reception outside of the body. In practice, the signals that are measured do not contain all the information necessary to completely characterize the internal body tissue, and some of the information contained in the signals is lost as a result of the signals not being received at all points in space. Therefore, an analytical "body model" is constructed for iteratively assessing different hypothetical characterizations and the respective theoretical effects on the signals that are actually measured, for comparison with the signals that are actually measured. This iteration results in convergence to a solution to the inverse problem within an acceptable bound of error.

It should be noted that the inverse problem is essentially the same problem encountered in imaging, except that there is generally no attempt in imaging to increase resolution by iterative use of an analytical body model. However, in all means of characterizing internal body tissue by probing the tissue from outside the body, there is ambiguity in the results and, to the same extent, a lack of resolution.

It is recognized herein that the diverse modalities and frequencies used in available imaging methods may be advantageously combined to greatly increase the resolution of the "image" or "solution" obtained from probing internal body tissue. It is also recognized that new probing methods are constantly being created, and it is therefore intended to apply the principles of the invention to conjoint application of any probing methods now available or later developed. Data obtained from one signal modality or frequency can be used to constrain the solution or inference obtained from another signal modality or frequency, such as in Bayesian analysis. On Bayesian analysis generally, see, e.g., Timothy C. Black et al., *Bayesian Data Analysis*, Computing in Science & Engineering, July/August 2001, pp 86–91; D. M. Schmidt et al. *Spatial-Temporal Bayesian Inference for MEG/EEG*, Human Brian Mapping 7, 195, 1999; Kevin H. Knuth, *Bayesian Source Separation and Localization*, In: A. Mohammad-Djafari (ed.), SPIE '98 Proceedings: Bayesian Inference for Inverse Problems, SPIE Vol. 3459, San Diego, July 1998, pp. 147–158.

An exemplary and preferred embodiment of the invention employs all three of the modalities mentioned above, i.e., electrical, acoustic, and electromagnetic modalities, and it is assumed for purposes of illustration that the frequencies of the signals transmitted within these modalities range substantially as indicated. However, it should be understood that more, or fewer, or different modalities may be employed, at any desired respective frequencies, without departing from the principles of the invention. In any event, by facilitating probing internal body tissue using multi-modal or multi-frequency signals, the present invention facilitates the extension of Bayesian constraints, resulting in faster and higher resolution solutions to the inverse problem.

The skin is an important barrier to the transmission and reception of many types of signals. While X-rays penetrate the skin so easily that the effects of the skin can be disregarded, it is recognized that electric, acoustic and optical electromagnetic signals must be carefully coupled to the skin in order to prevent excessive signal energy loss. Particularly, these particular modalities all require some form of physical contact with the skin. Generally, where a signal propagates from one medium to another (where the medium can be a vacuum in the case of electromagnetic signals), the signal is scattered or reflected at the interface between the media if the media have different impedances.

For coupling electric signals to the skin, it is important to have contact with the skin which minimizes electrical impedance at the frequency of the signal. For coupling acoustic signals to the skin, it is important to have contact with the skin which matches the acoustic impedance of the skin, which is proportional to the density of the skin. It is also believed to be novel to provide, as in the present invention, for coupling optical signals to the skin through a medium that matches the optical impedance of the skin, i.e., the index of refraction of the skin at the frequency of the light energy employed. As in other modalities, this provides more efficient coupling that increases signal strength. It is believed that such an interfacing medium has not been heretofore employed in the optical modality because of the expense and effort required, and the compensating recognition of coupling multi-modal signals according to the present invention has been lacking.

The coupling problem is relatively easily solved for a particular modality. In the electrical modality, highly electrically conductive electrodes are placed directly on the skin, and the interface can be improved by using an electrolytic solution or electrically conductive paste as an interfacing medium between the skin and the electrode. Skin (particularly scalp) tissue has a mean conductivity of 0.4 (ohm-meter)$^{-1}$ with a range of about 0.05 to 1.0. According to the invention, the interfacing medium preferably provides a conductivity that is at least as great as the maximum conductivity for skin of about 1.0 (ohm-meter)$^{-1}$.

In the acoustic modality, an oil or gel is typically used as the interfacing medium, where the oil or gel has an acoustic impedance that matches the acoustic impedance of the skin. Acoustic impedance is defined generally as the velocity of sound through the medium multiplied by the density of the medium. The acoustic impedance of skin is about 1.5+/− 0.15 kg/s-m$^2$ while that for air is four orders of magnitude smaller.

In the optical modality, according to the invention, an oil or gel may also be used as the interfacing medium, where the oil or gel has an index of refraction in the near-infrared that matches the index of refraction of the skin. Particularly, the refractive index of the oil or gel is about 1.5+/−0.15, as compared to air which has a refractive index of about 1.0.

In addition, according to the invention, it is desired to be able to couple multi-modal, multi-frequency signals to the skin, preferably simultaneously or contemporaneously. Referring to the FIGURE, this is facilitated by providing an interfacing medium or composition 10 that effectively conducts a plurality of signals having different modalities or frequencies. The medium 10 is applied to the skin 12 so that it makes intimate contact with the skin, and may be applied over hairs on the skin as shown if necessary. An optical probe 14 may be provided that makes intimate contact with the gel, such as by being immersed therein, for conducting optical signals. Similarly, an acoustic probe 16 and an electrode probe 18 may be provided that are in intimate contact with the gel for conducting acoustical signals and electric signals, respectively. Preferably all three probes are provided and are adapted to both transmit and receive (as emitter/receiver pairs) the respective signal types, but the probes may alternatively be adapted for just one or the other purpose.

Generally, the medium 10 should optimize impedance for at least two of the electrical, acoustic and optical modalities. For example, in a combination of electrical and acoustical modalities, the medium 10 is preferably optimized to have a minimum conductivity of about 1.0 $(\text{ohm-meter})^{-1}$ and an acoustic impedance of about 1.5+/−0.15 kg/s-m$^2$.

In a combination of electrical and optical modalities, the interfacing medium 10 is preferably optimized to have a minimum conductivity of about 1.0 $(\text{ohm-meter})^{-1}$ and a refractive index of about 1.5+/−0.15.

In a combination of acoustic and optical modalities, the interfacing medium 10 is preferably optimized to have an acoustic impedance of about 1.5+/−0.15 kg/s-m$^2$, and a refractive index of about 1.5+/−0.15. In a combination of electrical, acoustic and optical modalities, the medium 10 is preferably optimized to have a minimum conductivity of about 1.0 $(\text{ohm-meter})^{-1}$, an acoustic impedance of about 1.5+/−0.15 kg/s-m$^2$, and a refractive index of about 1.5+/−0.15.

According to the invention, the interfacing medium preferably comprises a hydrogel which may be supplemented as desired depending on the modalities employed. Where electrical modalities are employed, the hydrogel may be combined with ionic materials, e.g., $Na^+Cl^-$ or $K^+Cl^-$. For optical modalities, the hydrogel may be combined with oils such as glycerine to provide the desired optical properties. The hydrogel is preferably "thermoresponsive" so that it has a relatively low viscosity and can be easily manipulated at ambient temperature, but increases viscosity when it is warmed by the skin so that it becomes slightly adhesive to the skin. To provide additional adhesive properties, the hydrogel may include additional bonding agents.

As mentioned above, the diverse modalities as well as frequencies used in available imaging methods may be advantageously combined to greatly improve the quality and efficiency of imaging internal body tissue. This advantage may result from employing different signal modalities at the same locations, for solving the inverse problem, or from employing the different signal modalities at the same time, for imaging evanescent activity in the body such as neural currents.

In the preferred embodiment of the invention, the sensor net described in U.S. Pat. No. 5,291,888 to Tucker is used to harness selected "sets" of the probes, e.g., optical and acoustic, optical and electrical, acoustic and electrical, or optical, acoustic and electrical. The FIGURE shows a single set 20 of probes for the optical, acoustic and electrical modalities. The probes may each advantageously be supported on a pedestal as described in U.S. Pat. No. 5,348,006 also to Tucker, where the medium 10 is provided within the pedestal tube. Preferably, a full set of probes corresponding to a particular location on the skin are placed within the pedestal tube of a single pedestal, or if multiple pedestals are used, the probes of the set are placed as close to one another as practical, to provide, as much as possible, that the signals for each different probe type are transmitted or received at the same location. This facilitates correlating the data for the different modalities.

Preferably, sensors for optical, acoustic and electric signals (which may contain emitters, receivers, or emitter/receiver pairs) are combined into one structure ("sensor fusion"), which provides the advantages of minimizing spatial separation of the sensors, thus increasing correlation between the multi-modal data, decreasing manufacturing cost, and decreasing the time required to set-up the probing apparatus for use.

U.S. application Ser. No. 09/803,085 of Tucker and Tucker provides an example of employing multi-modal, multi-frequency signals for probing internal body tissue. Particularly, X-ray electromagnetic data is described as being employed to provide bone density information for use in combination with optical electromagnetic data and/or electrical data. Acoustic signals may also be employed, and therefore four or more independent data channels may be provided, i.e., two electromagnetic data channels (here X-rays and NIR light), one or more electrical data channels (corresponding to different frequencies of electrical stimulation), and an acoustic data channel.

For imaging soft tissue, an X-ray modality may be considered too invasive and may be omitted. However, a number of alternative modalities remain that can be used as inputs to a "body model" analytical simulation of body tissues such as explained in the '470 patent, to optimize convergence to solution of the inverse problem.

In addition, adaptive refinement may also be used in accordance with the invention, which is especially desirable for impedance characterization and source localization where impedance changes over time such that time for making measurements is a limited resource. Adaptive refinement focuses impedance characterization or source localization efforts on a particular sub-portion of the body volume. The capability provided by the present invention to more quickly converge to a solution of the inverse problem allows identifying a desired sub-portion quickly, by making relatively quick, gross impedance or source localization estimates. Thereafter, measurement resources can be applied more extensively to portions of the surface of the body proximate the desired sub-portion, thereby neglecting other portions of the body that are not of particular interest. This refining process can be carried out in any number of iterative steps.

It is to be recognized that, while a particular method and composition for probing the body through the skin has been shown and described as preferred, other configurations and methods could be utilized, in addition to those already mentioned, without departing from the principles of the invention.

The terms and expressions which have been employed in the foregoing specification are used therein as terms of description and not of limitation, and there is no intention in the use of such terms and expressions to exclude equivalents of the features shown and described or portions thereof, it being recognized that the scope of the invention is defined and limited only by the claims which follow.

The invention claimed is:

1. A method for probing interior portions of a body through the skin, comprising applying a coupling medium to the skin, and coupling, through said medium, (a) an electrical signal, and at least one of (b) an optical signal and (c) an acoustic signal in which case said medium has an acoustic impedance of 1.5+/−0.15 kg/s-m$^2$.

2. The method of claim 1, wherein said step of coupling couples said signals to the body substantially contemporaneously.

3. The method of claim 1, wherein said medium comprises a hydrogel.

4. The method of claim 3, wherein said hydrogel is thermoresponsive.

5. The method of claim 3, wherein said hydrogel has an acoustic impedance of about 1.5+/−0.15 kg/s-m$^2$, and a refractive index of about 1.5+/−0.15.

6. The method of claim 3, wherein said hydrogel has a minimum conductivity of about 1.0 (ohm-meter)$^{-1}$.

7. The method of claim 3, wherein said hydrogel has a minimum conductivity of about 1.0 (ohm-meter)$^{-1}$ and a refractive index of about 1.5+/1 0.15.

8. The method of claim 3, wherein said hydrogel has a minimum conductivity of about 1.0 (ohm-meter)$^{-1}$ and an acoustic impedance of about 1.5+/−0.15 kg/s-m$^2$.

9. The method of claim 8, wherein said hydrogel has a refractive index of about 1.5+/−0.15.

10. The method of claim 3, wherein said hydrogel has a refractive index of about 1.5+/−0.15.

11. The method of claim 4, wherein said step of coupling couples said signals to the body substantially contemporaneously.

12. The method of claim 11, comprising coupling through said medium, through the skin, at least (a) and (b).

13. The method of claim 11, comprising coupling through said medium, through the skin, at least (a) and (c).

14. The method of claim 2, comprising coupling through said medium, through the skin, at least (a) and (b).

15. The method of claim 2, comprising coupling through said medium, through the skin, at least (a) and (c).

16. The method of claim 1, comprising coupling through said medium, through the skin, at least (a) and (b).

17. The method of claim 1, comprising coupling through said medium, through the skin, at least (a) and (c).

18. A composition for probing interior portions of a body through the skin, comprising a hydrogel having a minimum conductivity of about 1.0 (ohm-meter)$^{-1}$ and a refractive index of about 1.5+/−0.15.

19. The composition of claim 18, wherein said hydrogel has an acoustic impedance of about 1.5+/−0.15 kg/s-m$^2$.

20. The composition of claim 18, wherein said hydrogel is thermoresponsive.

21. The composition of claim 19, wherein said hydrogel is thermoresponsive.

22. A composition for probing interior portions of a body through the skin, comprising a hydrogel having a minimum conductivity of about 1.0 (ohm-meter)$^{-1}$ and an acoustic impedance of 1.5+/−0.15 kg/s-m$^2$.

23. The composition of claim 22, wherein said hydrogel is thermoresponsive.

* * * * *